United States Patent [19]

Paul et al.

[11] Patent Number: 4,468,346

[45] Date of Patent: Aug. 28, 1984

[54] MONOCLONAL ANTIBODIES TO PORCINE IMMUNOGLOBULINS

[75] Inventors: Prem S. Paul; Richard A. Van Deusen, both of Ames, Iowa

[73] Assignee: The United States of America as represented by the Secretary of Agriculture, Washington, D.C.

[21] Appl. No.: 546,220

[22] Filed: Oct. 27, 1983

[51] Int. Cl.[3] ................. A61K 39/395; C12N 5/00; C12N 1/26; C12Q 1/00

[52] U.S. Cl. ............... 260/112 B; 260/112 R; 424/85; 435/7; 435/68; 435/69; 435/70; 435/172.2; 435/240; 435/241; 435/948; 436/548

[58] Field of Search ............ 260/112 R, 112 B; 424/85; 435/7, 68, 172, 240, 241, 948, 69, 70; 436/548

[56] References Cited

U.S. PATENT DOCUMENTS

| | | | |
|---|---|---|---|
| 4,070,453 | 1/1978 | Bordt et al. ............... | 435/240 X |
| 4,196,265 | 4/1980 | Koprowski et al. ........ | 435/68 X |
| 4,271,145 | 6/1981 | Wands et al. .............. | 424/85 |
| 4,350,683 | 9/1982 | Galfre et al. .............. | 424/85 |
| 4,361,549 | 11/1982 | Kung et al. ............... | 424/85 |
| 4,364,936 | 12/1982 | Kung et al. ............... | 424/85 |

FOREIGN PATENT DOCUMENTS 2075987  11/1981  United Kingdom ............... 435/172

OTHER PUBLICATIONS

Nature, 276: 269-270 (1978), Shulman et al.
R. A. Van Deusen et al., "Practical Aspects of Producing and Using Anti-Viral Monoclonal Antibodies as Diagnostic Reagents," Proc. Am. Assoc. Vet. Lab. Diagn. 24: 211-228 (1981).

*Primary Examiner*—Howard E. Schain
*Attorney, Agent, or Firm*—M. Howard Silverstein; David G. McConnell; Curtis P. Ribando

[57] ABSTRACT

Monoclonal antibodies which are heavy-chain specific for porcine Ig's are secreted by novel hybrid cell lines produced by fusing SP2/O myeloma cells with B-lymphocytes from BALB/c mice immunized against porcine Ig's. The monoclonal antibodies are useful in porcine immunological research and pathological diagnosis.

16 Claims, No Drawings

MONOCLONAL ANTIBODIES TO PORCINE IMMUNOGLOBULINS

BACKGROUND OF THE INVENTION

1. Field of the Invention

The pig has been used as an experimental model to study the ontogeny of fetal immune response because of its six-layered epitheliochorial placeta which prevents the passage of maternal immunoglobulins (Ig's) into the fetus and provides for an environment that is relatively sheltered from other exogenous antigens. Positive methods of detecting Ig's in the serum or other body fluids and Ig-containing cells in the tissues are paramount to such studies.

Immunoglobulin detection also holds considerable potential in porcine medicine. Immunoglobulin M (IgM) is the first and main Ig produced in an early primary immune response. Identification and quantitation of IgM could therefore be useful as a diagnostic technique for differentiating current from past infection. Immunoglobulin A (IgA) is the main Ig in secretions and excretions and plays an important role in secretory immunity especially to respiratory and enteric infectious agents.

The methods involved in these applications require monospecific antisera to Ig heavy chains at a level of specificity which heretofore has seldom been achieved in conventional preparations. For example, most preparations of purified IgM are commonly contaminated with trace amounts of $\alpha_2$-macroglobulins and antisera prepared to such IgM preparations contain antibodies to $\alpha_2$-macroglobulins. These antibodies are difficult to eliminate and tend to interfere with IgM detection even at very low concentrations. To obtain antisera to porcine IgM free of antibodies to both $\alpha_2$-macroglobulins and Ig light chains, it is necessary to extensively absorb the preparations with fetal-porcine serum devoid of Ig's and with heterologous Ig's.

This invention relates to the application of hybridoma technology to the preparation of cell lines capable of producing monoclonal antibodies (Mabs) to porcine Ig's having a high degree of heavy-chain specificity.

2. Description of the Prior Art

Fused cell hybrids of mouse myeloma cells with antibody-producing splenocytes have been widely utilized in recent years to produce Mabs to a variety of agents including, for example, viruses, antigens, cell-associated antigens, blood cells, enzymes, and other proteins. Illustrative of these are the array of hybrid cell lines for producing monospecific antibodies to cell-associated antigens disclosed by Kung et al. in U.S. Pat. Nos. 4,361,449, 4,361,550, and 4,364,932-'937. As another example of this technology, Wands et al., U.S. Pat. No. 4,271,145, fuses BALB/c mouse myeloma cells with BALB/c lymphocytes to yield hybridoma cell lines which secrete highly specific IgG or IgM Mabs to hepatitis virus antigen.

It is apparent from the discussion in the "Field of the Invention" that antibody to porcine Ig's having the specificity achieved by the Mabs of the prior art would be an advantageous tool to both immunological research and porcine diagnostic medicine.

SUMMARY OF THE INVENTION

We have now succeeded in producing Mabs which are specific for heavy chains of porcine Ig's. The Mabs to porcine IgM are $\mu$-chain specific and form a single precipitin ring against porcine serum in the radial immunodiffusion test. In immunodiffusion and immunoelectrophoresis tests, they form a single precipitin line with porcine serum and IgM and no lines of precipitation with porcine IgG, IgA or fetal porcine serum. In the indirect enzyme-linked immunosorbent assay (ELISA), the monoclonal antibodies react with porcine IgM, $\mu$-chains and porcine serum, and not with IgG, IgA or light chains. These antibodies recognize two distinct antigenic sites on porcine-IgM in competitive ELISA and have mouse $IgG_1$, kappa isotype. The Mabs to porcine IgG are $\gamma$-chain specific and do not react with porcine IgM, porcine IgA, or light chains. Likewise, Mabs have been produced to porcine IgA which are $\alpha$-chain specific.

The antibodies of this invention are secreted by hybrid cell lines generated by fusing mouse myeloma cells with splenic B-lymphocytes from a mouse immunized with porcine Ig. While the general method of obtaining hybrid cell lines is well established, the technology is unpredictable in terms of isolating a line for producing a specific antibody of predetermined reactivity. We were therefore surprised to succeed in isolating a number of hybridomas which secrete Mabs to porcine Ig's.

In accordance with this discovery, it is an object of the invention to produce heavy-chain specific Mabs to porcine Ig's.

It is also an object of the invention to establish stable, continuously proliferating hybrid cell lines as sources for the subject antibodies.

It is a further object of the invention to culture the established hybrid cell lines of the invention either in vitro or in vivo for the purpose of producing the subject antibodies.

Another object of the invention is to provide a method for producing relatively large quantities of antiporcine Ig's without the need for the immunization and purification procedures characteristic of conventional methods.

Still another object of the invention is to provide heavy-chain specific Mabs useful in porcine immunological research and pathological diagnosis.

Other objects and advantages of the invention will become readily apparent from the ensuing description.

DETAILED DESCRIPTION OF THE INVENTION

Establishing the antibody-secreting cell lines for use in the invention is a multistep procedure which includes immunizing a mouse to induce a proliferation of antibody-producing spleen cells, promoting fusion between the spleen cells and cells of a mouse myeloma, selecting for antibody-secreting hybridomas, and cloning the selected hybridomas. The clones are maintained as cell lines and cultured for antibody production.

The myeloma cell line chosen for fusion is most desirably one which does not itself secrete antibody. A preferred myeloma is the SP2/0 cell line established from a BALB/c mouse by Shulman et al. [Nature 276:269-270 (Nov. 16, 1978)]. An objective of this procedure is to maximize the number of myeloma cells and spleen cells in metaphase at the time of fusion. This is accomplished for the myeloma cells by passaging the line on a suitable growth medium according to a schedule allowing for the log phase to coincide with the fusion date. The cell line is also passaged two or three times at 4- to 8-week intervals on a growth medium containing 8-azaguanine or the like for the purpose of maintaining susceptibility to a screening agent during the hybridoma selection, as described in further detail below.

Spleen cells primed for a given anti-Ig production are obtained from mice previously immunized with the corresponding porcine Ig type. The particular Ig material used for immunization is not especially critical. For example, a suitable source for IgM is pig serum from an animal in the IgM phase of response to an injected antigen. Colostral whey and milk whey can serve as a suitable source for IgG and IgA, respectively. Of course, it should be apparent that the purer the Ig material used for immunization, the more specific the splenocyte response and the more facile the subsequent hybridoma selection process.

The syngeneic nature of the fusion dictates that the splenocyte donor be genetically identical to the myeloma cell line for maximum efficiency. Thus, for fusion with the SP2/0 line, a mouse of the BALB/c strain is preferred. Either sex of mouse may be used.

The ideal immunization schedule in terms of productive hybridization is a two-step process in which the mouse is first inoculated intraperitoneally and then hyperimmunized 4 to 21 days later by intravenous injection. The initial inoculation stimulates the B-lymphocytes of the spleen to produce the anti-Ig antibodies, and the latter stimulates further cell multiplication. For maximizing the number of B-lymphocytes in metaphase, hyperimmunization should be scheduled on the third day prior to fusion. Determination of the optimum dose of Ig would be within the skill of a person in the art, though 0.2 mg per injection has proven effective.

On the day of fusion, the spleen cells of the immunized mouse are harvested and cosuspended in a suitable growth medium with the myeloma cells in a preferred ratio of myeloma:B-lymphocytes in the range of about 1:1 to 2:1. After concentrating the cell suspension by centrifugation or other convenient method, the cell mixture is incubated at about 37° C. in the presence of a fusion promoter such as polyethylene glycol (PEG). Commercial PEG 1540 having a molecular weight in the range of 1300–1600 is preferred though others having molecular weights in the range of 1000–4000 are also effective. Incubation is continued for 1–2 min or until the cells have coalesced. The fusion is thereafter halted by dilution with growth medium and concentration of the cells.

The cells recovered from the fusion process are plated in a selective medium containing the screening agent against unfused myeloma cells and myeloma x myeloma fusions. The conventional medium for this purpose is HAT (hypoxanthine, aminopterin, and thymidine) in which the aminopterin functions as the screening agent in that it kills the susceptible myeloma cells. Alternatively, analogs of aminopterin, such as methotrexate, can be used as the agent. The unfused spleen cells and spleen x spleen fusions will cease to proliferate after about 1 week's time. In a normal workup, the cells in the selective medium are cultured at about 37° C. in a $CO_2$-enriched atmosphere at high humidity for 10–14 days. Medium is periodically screened for antibody production and replenished as necessary. Applicable screening tests for hybridoma selection include radial immunodiffusion, immunoelectrophoresis, enzyme-linked immunosorbent assay (ELISA), and indirect ELISA. The selected primary (1°) hybrids are serially passaged into larger wells or into flasks as cell numbers increase.

The 1° hybrids are cloned to insure that all progeny secrete the desired antibody. Cloning is accomplished by plating or otherwise propagating individual cells selected from the chosen hybridomas. Antibody is most expeditiously produced in vivo by injecting cloned cells into a syngeneic host and periodically collecting the ascites fluid. Up to about 20% of the antibody recovered from the ascites fluid may be of host origin, but typically these extraneous host antibodies will not interfere with the proposed applications of the anti-porcine Ig's. Alternatively, the cloned cells are cultured in vitro in a suitable growth medium, and the antibody is recovered from the supernatant fluid.

The following examples are intended only to further illustrate the invention and is not intended to limit the scope of the invention which is defined by the claims.

EXAMPLE 1

Hybridomas for producing Mabs to porcine IgM are prepared and cloned following the general procedure of Van Deusen and Whetstone [Proc. Am. Assoc. Vet. Lab. Diagn. 24:211–228 (1981)], herein incorporated by reference, as outlined below. The media preparation utilized for the procedure included the following:

Dulbecco's minimal essential medium (DMEM).

Basic nutrient medium (BNM) is DMEM plus 4500 mg/l of glucose.

DMEM-R or regular growth medium is prepared by adding 75 ml of 2 parts agammaglobulin horse serum and 1 part SPF (bovine virus diarrhea virus free) calf serum (Hy-serum) to 925 ml of BNM, then adding 50 mg gentamicin.

DMEN-F consists of DMEN-R with 100 mcg/l of "Fungazone" (Amphotericin B, GIBCO Laboratories).

DMEM-CF is prepared by adding 200 ml of Hy-serum to 800 ml of BNM and then adding 50 mg of gentamicin.

DMEN-8-aza is DMEN-R made up with 2 mg/l 8-azaguanine and combined with Hy-serum in the ratio of 925 ml of medium to 75 ml Hy-serum. Fifty mg/l of gentamicin is added to the combined medium.

Conditioned medium (CM) is prepared by harvesting medium by centrifugation in which SP2/0 cells have been growing for 2 to 3 days.

HAT was made substituting methotrexate for aminopterin by combining hypoxanthine solution (68 mg in 100 ml of distilled $H_2O$), methotrexate solution (0.1 ml in 9.9 ml of distilled $H_2O$), and thymidine solution (2.42 mg in 10 ml of distilled $H_2O$).

H-T, or hypoxanthine and thymidine solution, is made by omitting methotrexate from the HAT solution above.

HAT medium is prepared by mixing together 50 ml each of DMEM-F and CM, then adding 1.2 ml of HAT solution.

H-T medium is prepared by mixing together 50 ml each of DMEM-F and CM, and then adding 1.1 ml of H-T solution.

Immunization of spleen donor

A BALB/c female mouse was inoculated intraperitoneally with 0.2 mg of porcine IgM, which had been previously isolated and purified from porcine serum by a combination of ion exchange chromatography and gel filtration. After 21 days, the mouse was reinoculated intravenously with 0.2 mg of the porcine IgM and then exsanguinated 3 days later. The spleen was removed, crushed through an 80-mesh sieve and the cells suspended in 3.5 ml DMEM.

Preparation of myeloma cells

The SP2/0 cell line established by Shulman et al., was maintained in continuous culture by 2 to 3 times weekly passage at a 1:10 ratio in regular growth medium, DMEM-R. The cells were grown in plastic flasks with loosened caps kept at 37° C. with 5–7% $CO_2$. Aminopterin susceptibility was maintained by two or three passages in DMEM-8-aza at 4- to 8-week intervals.

Fusion of cells

The SP2/0 cells were resuspended in DMEM and mixed with the spleen cell suspension in a ratio of SP2/0:spleen cells of 2:1. The resultant cell suspension was concentrated by centrifuging at 200×g for 8 min and removing the supernatant by decantation from the pellet of cells at the tip of the centrifuge tube. By shaking the tube, the cells were dispersed in the remaining medium. Fusion was initiated by slowly adding PEG 1540, gently mixing, and incubating in a water bath at 37° C. for 90 sec. Dilution with DMEM halted the effect of the PEG on the cell membranes and the cells were thereafter recovered by centrifugation. The cells were then diluted with HAT medium to the equivalent of $5 \times 10^5$ myeloma cells/ml, and two-thirds of the suspension was dispensed into 96-well microtiter plates, 0.2 ml/well. The remaining one-third was diluted with an equal amount of HAT medium and plated in a similar manner. Incubation was conducted at 37° C., 5–7% $CO_2$, and high humidity. The wells were periodically examined with an inverted microscope for 1° hybrid colonies and fresh HAT medium added as necessary. Culture fluids were screened at various intervals for production of antibodies to porcine IgM.

Cloning primary hybrids

The antibody-secreting 1° hybrids were cloned by the limiting dilution method in which mixtures of SP2/0 myeloma cells and 1° hybrid cells were plated in a 166,000:1 ratio in HAT medium at a 1° hybrid cell concentration of 3 cells/ml. The purpose of the SP2/0 cells was to sufficiently disperse the 1° hybrid cells so as to obtain isolated clones. The cell suspensions were then plated by dispensing four drops from a 5-ml pipette into each well of a 96-well plate and incubated at 37° C. in 5–7% $CO_2$. Wells with single clones were sampled for antibody production and fed with H-T medium. Productive clones were successively moved up to 48-well plates and 24-well plates in H-T medium for expansion as required.

Ascites fluid production

Monoclonal antibodies were produced in vivo using a female BALB/c mouse of at least 5 months of age and primed 3 weeks prior to use by intraperitoneal administration of 0.5 ml of pristane (2,6,10,14-tetramethylpentadecane). Cells from each of the cloned hybridomas were implanted into the mouse by injecting 1.0 ml of actively growing clone cells (about $1 \times 10^6$ cells/ml) into the peritoneal cavity of the recipient mouse. When abdominal swelling became pronounced, ascites fluid was aspirated with disposable myelography needle and a 10-ml syringe. Repeated harvests were made at 2- to 3-day intervals until the mouse died. Each fluid harvest was clarified by centrifugation.

Assay procedures employed in this example were as follows:

Radial immunodiffusion

Five ml of 0.8% agarose in 0.02 M sodium borate buffer, pH 8.6 containing either 1:50 or 1:200 dilution of porcine serum was poured on a microscopic slide. Twenty wells with a diameter of 2.5 mm were cut and 5 $\mu$l samples were placed in wells. Goat antiporcine IgM antiserum was used as a positive control in each slide. The slides were incubated at room temperature in a humid chamber and examined at 24 and 48 hr for immunoprecipitin rings. After 48 hr, the slides were washed in normal saline, pressed, dried, and stained with "Commassie blue R250" and reexamined.

Indirect ELISA

Wells of polystyrene 96-well flat-bottom microtiter plates ("Immulon II," Dynatech Laboratories, Inc.) were coated with procine IgM (1 $\mu$g/ml), $\mu$-chains (1 $\mu$g/ml), IgG (100 ng/ml), IgA (1 $\mu$g/ml), light chains (1 $\mu$g/ml) or serum from various animal species at 1:100 dilution by adding 0.2 ml of protein solutions per well in 0.1 M carbonate-bicarbonate buffer, pH 9.6 and incubated at 4° C. overnight. The plates were washed three times with phosphate buffered saline (PBS) containing 0.01% Tween-20 (PBS-Tween). The plates were incubated for 1 hr at room temperature with PBS containing 1% bovine serum albumin (BSA) to block remaining sites and the plates were washed again. Culture fluids from primary hybrids were diluted 1:10 in PBS-Tween containing 1% BSA (PBS-Tween-BSA) and 0.2 ml were added to each well. The plates were incubated for 2 hr at room temperature and washed with PBS-Tween. A 0.2-ml volume of an optimal dilution of horseradish peroxidase-labeled anti-mouse IgG, heavy and light chains conjugate (Cappel Laboratories) was added to each well. The conjugate had been passed over a sepharose 4B-porcine IgG column to remove antibodies cross reacting with porcine IgG. The plates were incubated at room temperature for 2 hr and then washed three times with PBS-Tween. A 0.2 ml of substrate-chromogen solution consisting of 2 mM hydrogen peroxide and 0.2 mM "ABTS" [2,2'-azino-di-(3-ethyl-benzythiazoline sulfonic acid)] in 0.5 M citrate buffer, pH 4.0 was added to each well. The absorbance was recorded at 405 nm in an automatic ELISA reader (Dynatech 580, Dynatech Laboratories).

Immunodiffusion and immunoelectrophoresis

These were performed on 84×90 mm glass plates using 12 ml of 0.8% agarose (Seakem Laboratories) or 1.5% "Noble" agar (Difco Laboratories) in 0.02 M borate buffer, pH 8.6 for immunodiffusion and immunoelectrophoresis, respectively. For immunodiffusion, 4-mm wells were cut and the distance between the central and peripheral wells was 4 mm. Approximately 15 $\mu$l of an appropriate dilution of sample was placed in each well. For immunoelectrophoresis, size of the wells was 2.5 mm in diameter. Electrophoresis was performed at 100 volts at 4° C. for 2 hr. Troughs were cut and 100 $\mu$l of appropriate dilutions of antiserum were added. Both immunodiffusion and immunoelectrophoresis plates were incubated at room temperature for 48 hr, washed, pressed, dried, and stained.

Preparation of horseradish peroxidase conjugates

Globulins were precipitated from clarified ascites fluids at 50% saturation of ammonium sulphate and Ig's were isolated by ion-exchange chromatography using a linear gradient of 20 mM Tris HCl, pH 7.8 containing 20 mM NaCl and 40 mM Tris HCl, pH 7.8 containing 400 mM NaCl. Immunoglobulin fractions containing the antibody activity were conjugated with horseradish peroxidase by the periodate method.

Competitive ELISA

Microtiter plates were coated with porcine IgM and treated with PBS-BSA as described for indirect ELISA. Dilutions of ascitic fluids in PBS-Tween-BSA were mixed with equal amounts of an optimal dilution of horseradish peroxidase conjugated antiporcine IgM and a 0.2-ml of the mixture added to each of two wells in an IgM-coated plate. Conjugate mixed with equal amounts of PBS-BSA served as a control. After 2 hr of incubation at room temperature, the plates were washed and the amount of conjugate bound to the solid phase was determined as in indirect ELISA.

Immunoglobulin isotyping

Culture fluids from cloned hybrid lines were tested for mouse Ig isotypes in an indirect ELISA using an isotyping kit (Boehringer-Manheim). Culture fluids concentrated 5 to 10 times by ammonium sulphate precipitation were also tested in immunodiffusion test using anti-Ig isotype antisera (Litton Bionetics, Kensington, MD).

Characterization of antibodies

Two hundred and thirty-one primary hybrids were obtained by virtue of the fusion procedure described above. In initial screening, culture fluids of 79 of these 1° hybrids were positive in indirect ELISA using porcine IgM as an antigen, and 11 of the 1° hybrids formed precipitin rings in radial immunodiffusion against porcine serum. All but one of the 1° hybrids that secreted precipitating antibodies were also positive in IgM-ELISA. Four of the hybrids that were positive in ELISA and radial immunodiffusion stopped secreting antibodies within a month following fusion. The remaining six 1° hybrids designated 1A11, 1D10, 2D7, 2E2, 3B11, and 5C9 were selected for cloning.

The specificity and reactivity of the monoclonal antibodies in the collected ascites fluids of the six cloned hybrids were characterized. In each case the Mabs were mouse IgG₁ heavy chain, kappa light chain isotype by both immunodiffusion and indirect ELISA. Also in each case, the Mabs formed single precipitin lines against porcine serum and porcine IgM and no lines against porcine IgG, IgA, or fetal porcine serum in immunodiffusion. The precipitin lines between the Mabs and porcine serum formed lines of identity with those formed between porcine serum and polyclonal goat anti-porcine IgM antiserum, and also with those formed between porcine serum and goat anti-human IgM antiserum. In immunoelectrophoresis, all of the six Mabs formed single precipitin lines with porcine serum which were characteristic of IgM. Similar lines were observed with porcine IgM; however, no lines were observed with IgG or IgA. None of the six Mabs reacted with human, cow, sheep, goat, dog, rabbit, guinea pig, or chicken serum in immunodiffusion or indirect ELISA. These antibodies were therefore all μ-chain and species specific.

Epitope specificities of the Mabs were determined by competitive ELISA. Mabs 1A11, 1D10, 2D7, 2E2, and 3B11 competed with horseradish peroxidase (HRP)-conjugated 1A11, but not with HRP-conjugated 5C9. Similarly Mab 5C9 competed with HRP-conjugated 5C9, but not with HRP-conjugated 1A11, 1D10, 2D7, 2E2, or 3B11. These results suggested that 5C9 Mab recognizes a different antigenic determinant than those recognized by the other five Mabs. Antibodies 1A11, 1D10, 2D7, 2E2, and 3B11 either recognized the same antigenic determinant or interfered with one another in recognizing distinct antigenic determinants.

Cloned hybrid cell line 5C9 has been deposited in the American Type Culture Collection in Rockville, MD, and assigned Accession No. ATCC HB 8371. The remaining cell lines disclosed herein as well as other cell lines which are produced by the disclosed method and which secrete Mabs to porcine Ig's are considered to be equivalent to cloned cell 5C9 for purposes of the invention, regardless of epitope specificity. Such equivalent cell lines as well as the antibodies produced thereby are accordingly deemed to be within the scope of the invention.

EXAMPLE 2

Hybridomas for producing Mabs to porcine IgG were prepared, cloned, and characterized following the general procedures described in Example 1 except that the source of splenic immunocytes was a mouse immunized with porcine IgG. Resultant cloned hybridomas 2A9 and 3H2 secreted Mabs specific for γ-chain of porcine Ig.

EXAMPLE 3

Hybridomas for producing Mabs to porcine IgG were prepared, cloned, and characterized following the general procedures described in Example 1 except that the source of splenic immunocytes was a mouse immunized with porcine IgG and the hyperimmunizing dose was administered at 4 days following the initial immunization. Resultant 1° hybrids 1C6, 1E6, 1G7, 1H7, 2B4, 2C6, 3F11, 3H10, 4A1, 4A7, and 4H8 and cloned hybridomas 1B4 and 1F9 secreted Mabs specific for γ-chain of porcine Ig. Antibodies secreted by one of the cloned hybridomas, 1F9, are of mouse IgM isotype.

EXAMPLE 4

Hybridomas for producing Mabs to porcine IgA were prepared and characterized following the general procedures described in Example 1 except that the source of splenic immunocytes was a mouse immunized with porcine IgA. Resultant 1° hybrids 2A7 and 4E8 secreted Mabs specific for α-chain of porcine Ig.

It is understood that the foregoing detailed description is given merely by way of illustration and that modification and variations may be made therein without departing from the spirit and scope of the invention.

We claim:

1. Monoclonal antibody which is heavy-chain specific for porcine immunoglobulin.

2. Monoclonal antibody as described in claim 1 which is μ-chain specific.

3. Monoclonal antibody as described in claim 1 which is γ-chain specific.

4. Monoclonal antibody as described in claim 1 which is α-chain specific.

5. Monoclonal antibody as described in claim 1 produced by a hybridoma generated by fusing mouse myeloma cells with splenic B-lymphocytes from a mouse immunized with porcine immunoglobulin.

6. Monoclonal antibody as described in claim 1 produced by a hybridoma generated by fusing SP2/0 myeloma cells with splenic lymphocytes from a BALB/c mouse immunized with porcine immunoglobulin.

7. A method of preparing monoclonal antibody which is heavy-chain specific for a predetermined porcine immunoglobulin type comprising culturing in vitro a hybridoma generated by fusing mouse myeloma cells with splenic B-lymphocytes from a mouse immunized with said porcine immunoglobulin type, and collecting from said culture the supernatant fluid containing the antibody.

8. A method of preparing monoclonal antibody as described in claim 7 wherein said immunoglobulin type is IgM and said antibody is $\gamma$-chain specific.

9. A method of preparing monoclonal antibody as described in claim 7 wherein said immunoglobulin type is IgG and said antibody is $\beta$-chain specific.

10. A method of preparing monoclonal antibody as described in claim 7 wherein said immunoglobulin type is IgA and said antibody is $\alpha$-chain specific.

11. Monoclonal antibody prepared by the method of claim 7.

12. A method of preparing monoclonal antibody which is heavy-chain specific for a predetermined porcine immunoglobulin type comprising injecting a mouse intraperitoneally with a hybridoma generated by fusing mouse myeloma cells with splenic lymphocytes from a mouse immunized with said porcine immunoglobulin type, and collecting from said mouse the ascites fluid containing the antibody.

13. A method of preparing monoclonal antibody as described in claim 12 wherein said immunoglobulin type is IgM and said antibody is $\mu$-chain specific.

14. A method of preparing monoclonal antibody as described in claim 12 wherein said immunoglobulin type is IgG and said antibody is $\gamma$-chain specific.

15. A method of preparing monoclonal antibody as described in claim 12 wherein said immunoglobulin type is IgA and said antibody is $\alpha$-chain specific.

16. Monoclonal antibody prepared by the method of claim 12.

* * * * *